(12) United States Patent
Ranalli

(10) Patent No.: US 6,634,883 B2
(45) Date of Patent: Oct. 21, 2003

(54) DEVICE FOR DESIGNING AND FURTHER IMPLANTING A DENTAL IMPLANT, METHOD FOR PLANNING CORRECT IMPLANTATION OF A DENTAL IMPLANT USING SAID DEVICE, AND PRE-TOMOGRAPHIC GUIDE AND SURGICAL TEMPLATE OBTAINED WITH SAID METHOD

(76) Inventor: Sebastian Luciano Ranalli, Marcelo T. de Alvear 2149, 3 fl. "A", Buenos Aires (AR), 1122

( * ) Notice: Subject to any disclaimer, the term of this patent is extended or adjusted under 35 U.S.C. 154(b) by 0 days.

(21) Appl. No.: 09/880,884

(22) Filed: Jun. 15, 2001

(65) Prior Publication Data

US 2001/0053510 A1 Dec. 20, 2001

(30) Foreign Application Priority Data

Jun. 16, 2000 (AR) ..................... P 00 01 02996

(51) Int. Cl.[7] .............................. A61C 3/00; A61C 3/06
(52) U.S. Cl. ............................... 433/50; 433/51; 433/75
(58) Field of Search .................. 433/173, 174, 433/175, 176, 50, 51, 55, 72, 75, 76

(56) References Cited

U.S. PATENT DOCUMENTS

| | | | | |
|---|---|---|---|---|
| 4,493,644 A | * | 1/1985 | Ai et al. | 433/75 |
| 5,222,892 A | * | 6/1993 | Perry | 433/75 |
| 5,551,873 A | * | 9/1996 | Aiba | 433/72 |
| 5,556,278 A | * | 9/1996 | Meitner | 433/75 |
| 6,050,816 A | * | 4/2000 | Phoenix et al. | 433/55 |
| 6,186,781 B1 | * | 2/2001 | Iba | 433/50 |
| 6,250,919 B1 | * | 6/2001 | Haje | 433/50 |
| 6,319,006 B1 | * | 11/2001 | Scherer et al. | 433/215 |

* cited by examiner

Primary Examiner—Cary E. O'Connor
(74) Attorney, Agent, or Firm—Wiggin & Dana LLP; Gregory S. Rosenblatt; Alberta A. Vitale

(57) ABSTRACT

A device for planning and further placing a dental implant comprises a rigid base, a column that projects from the base with a regulating mechanism for the height and support of a bi-directional head. The head has two hubs, which have binding mechanisms for certain positions and are furnished with a mechanism for indicating the angle position. One of the hubs is furnished with a drill and also a device for fixing guides. Also described and claimed are a method for planning correct placing of a dental implant, a pre-tomographic guide obtained with the method, and a surgical template obtained using the method.

10 Claims, 4 Drawing Sheets

DEVICE FOR DESIGNING AND FURTHER IMPLANTING A DENTAL IMPLANT, METHOD FOR PLANNING CORRECT IMPLANTATION OF A DENTAL IMPLANT USING SAID DEVICE, AND PRE-TOMOGRAPHIC GUIDE AND SURGICAL TEMPLATE OBTAINED WITH SAID METHOD

FIELD OF THE INVENTION

The present invention relates to a device, which makes it possible to guide the placing of dental implants, which usage involves completely novel concepts, rendering remarkable advantages over the systems known in the art.

BACKGROUND OF THE INVENTION

Dental implant is an ancient art through which missing dental pieces are replaced, and it is a solution that man found long time ago. In effect, even during Egyptian times attempts were made to replace dental pieces for scoured pieces, fitted immediately after the original piece was removed.

Since those times, many improvements have been made, including the development of prosthesis and bridges to replace missing pieces.

Likewise, osseointegration process has been studied and developed for the last twenty-five years. In this process, several materials suitable for implantation in jawbones without bone-rejection have been developed and tested. One of the materials tested that resulted to be relatively successful is titanium and alloys from it. With these materials, screw-shaped pieces have been fabricated, the pieces being screwed in the bone after a hole is drilled for fitting said screw. But in practice there is a percentage of rejections, the reason for many of which is lack of planning, and this is troublesome for the patient and also causes a deep feeling of frustration for the dentist applying said surgical practice.

Continuous, deep study of the foregoing drawbacks encountered in implants resulted in the confirmation that it was extremely important to determine the exact place where the hole must be drilled on the maxilla bone (hereinafter referred to as incidence point), and the tilt thereof (hereinafter referred to as incidence angle). For this purpose, different radiographic tests have been used in order to study—prior to any surgery—all special parameters of the maxilla bone of each patient, so as to minimize rejection risks. Said radiographic tests include panoramic x-ray, which provide a complete view of maxilla and teeth.

However the use of these x-ray plates provides a first approach to study the morphology of the jaw bone of the patient to be implanted, in practice they result to be insufficient, as any radiography implies a flat image and also presents a certain deformation from actual sizes, which is a drawback for suitable anchoring of the implant as it prevents specifying the accurate position or coordinates for the implant. Said deformation of actual image varies upon the equipment used, but in most cases it leads to a deformation ranging form 20 to 50%, which is clearly unacceptable for practicing a high precision surgery.

As already mentioned, another important issue to be taken into account is the tilt of the hole where the implant is placed. This tilt is directly related to characteristics of the jaw bone where in implant is placed, which changes from one patient to another, and from one tooth to another in the same patient; so in each case the incidence angle must be accurately specified, so as to be sure that neither proximate cavities nor nerves would result injured, causing an irreparable damage for the patient.

SUMMARY OF THE INVENTION

The device and method of this invention have been developed for overcoming the foregoing drawbacks, the use of which allows for a completely accurate placing of the implant. For this method, a computed tomography is necessary, or either any other radio-diagnostic test which, along with the use of a planning device, renders a template with correct incidence points and angles.

Through computed tomography, axial and transversal cross sections may be observed, as well as panoramic views of the patient's mouth, all of them without deformation, so the profile of the jaw bone where the implant is to be placed is clearly seen.

On its side, by using the device of the present invention, it is possible to exactly specify the tilt that must be considered for each implant, using the information provided by said tomography. The whole process shall be taught hereinafter.

The use of the proposed device and method implies several improvements, which may be summarized as follows:

1) a correct planning of the implant is achieved, which reduces to a minimum any risk associated to surgery;
2) in most cases, an unexposed surgery is favored, which results completely non-bloody for the patient, and the post-surgery stage is almost unnoticed;
3) in case the patient has an irregular jaw bone and gum tissue must be cut and lifted for working over the jaw bone, the method is also useful for keeping planning constant throughout surgery;
4) it greatly reduces time spent in the surgical setting;
5) by using the method, the implant is more safely distributed, and positioning results more accurate, which undoubtedly facilitates the job of the restorative dentist when fabricating the prosthesis;
6) having a highly accurate tool for this type of surgeries, negligence or unskillfullness, which are frequent in today dental implant practice, are almost negligible.

One of the main objects of the proposed device is to obtain a plate, called "surgical template", which is useful for transferring the planning into a patient mouth, and said planning is kept constant during surgery, so exploratory surgeries in the maxilla having so many vital elements, are avoided.

Said surgical template defines a guide which provides the professional with exact incidence angle and point where the hole is to be drilled, for further anchoring the implant.

Basically, the device of the present invention allows for the preparation of a pre-tomographic guide with radio opaque elements, so as to have a full, accurate view of the computed tomography details and the surgical template, which will be placed into the patient when he/she is subject to surgery.

Moreover, this invention provides a method, which basically comprises the following stages:

1) preparing a pre-tomographic guide with an impression (mouth model), through which a plaster—or similar material'model of the patient mouth is made, and also a diagnostic replica piece (a scale model of the prosthesis). By using a traditional duplicator, a reproduction of the replica piece is made in a polymer material, such as acrylic or any other like transparent material; also the knot of a polymeric material, such as acrylic or the like, may be employed; the replica is placed in said model and with a specially designed device holes are drilled at the position of each dental piece, measuring the incidence angle both, mesio-distal and mouth-palatine/lingual, the values being logged in a sheet. A radio opaque substance is introduced in each hole, thus determining pre-tomography guide;

2) taking a computer tomography with the patient having the pre-tomographic guide in his mouth;

3) making a computer-assisted planning with a specially designed software (which is a surgery simulator), with which it is possible to see tomographic cross sections of the maxilla bone, and over them a white line corresponding to the radio opaque substance of the guide where we have registered the estimated incidence angles, incidence angle and incidence point are rectified, and new values are logged;

4) making a surgical template (which serves for transferring the planning with corrections into the patient's mouth), using the aforementioned device, which allows for metal guides be placed over an acrylic plate in all positions where each implant will be placed, having corrected incidence angle and point;

5) placing the template obtained in step 4) into the patient mouth, and placing the implant following the steps already known for this process.

This means that the drill is inserted into the metal guides already mentioned, so the hole in the patient jaw bone has the predetermined incidence point and tilt with the above advantages.

In fact, the features and improvements mentioned above are only a few of the characteristics of the present invention, which will be more clearly understood as the present description proceeds, when taken in conjunction with the accompanying drawings, which are merely exemplary of the invention, and not limitative in any way.

DETAILED DESCRIPTION OF PREFERRED EMBODIMENTS

Figure 1:
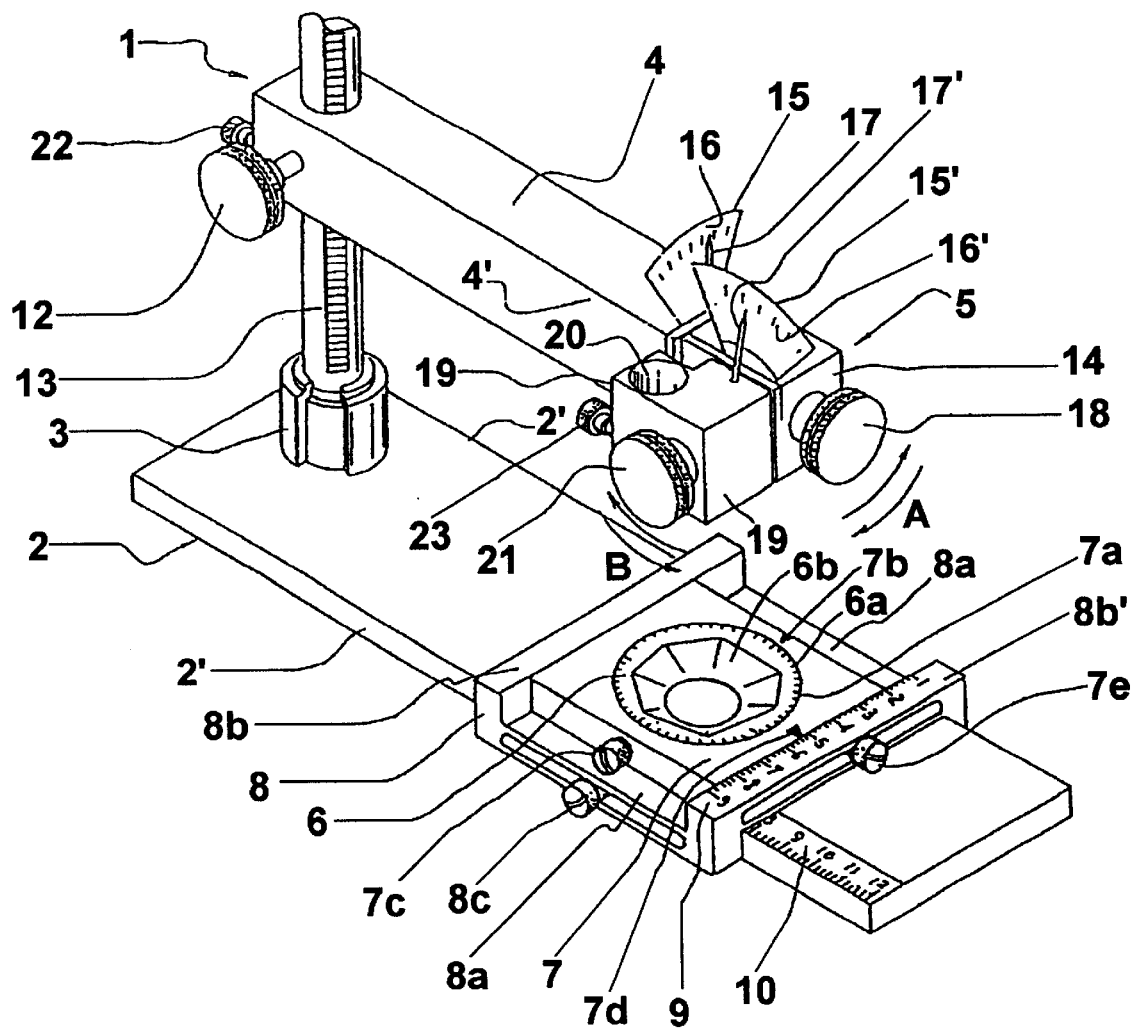
FIG. 1 is a perspective view of an embodiment of the device of this invention, when the proposed angulator device fixes metal guides on the acrylic plate in each position where the implant is to be placed, having corrected angulation and incidence point.
Figure 2:
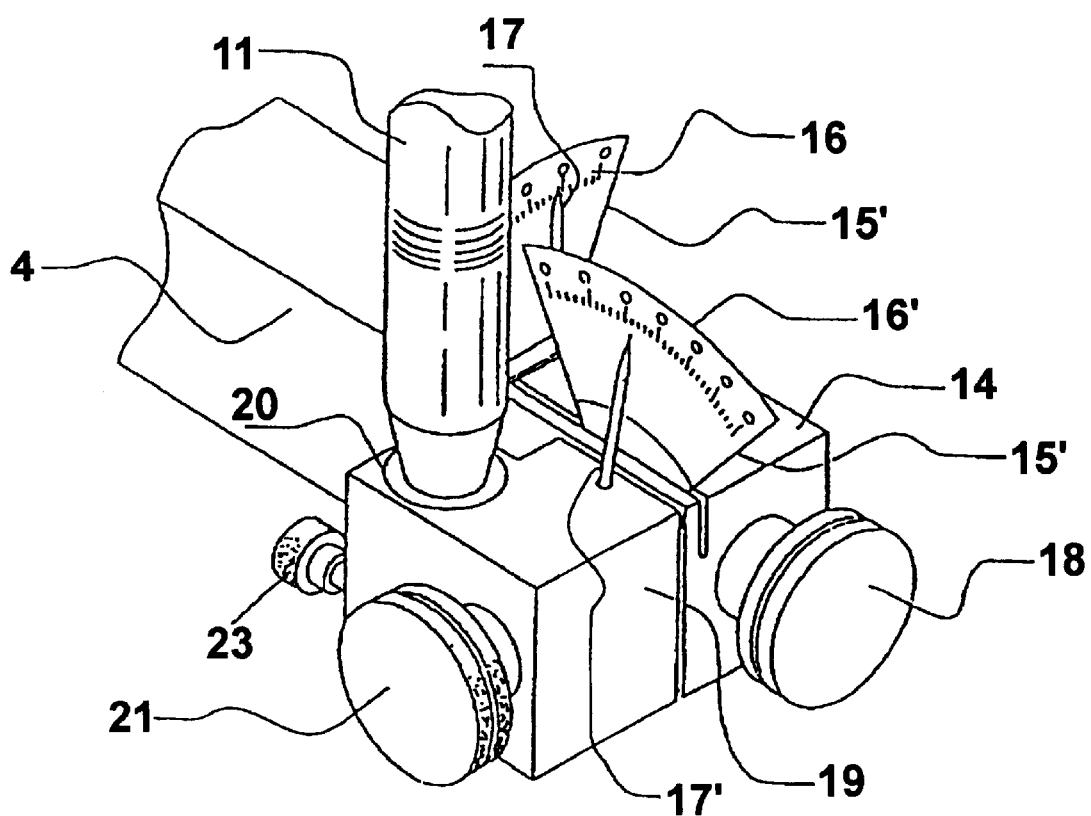
FIG. 2 is another perspective view showing a detailed embodiment of the above bi-directional head.
Figure 3A:
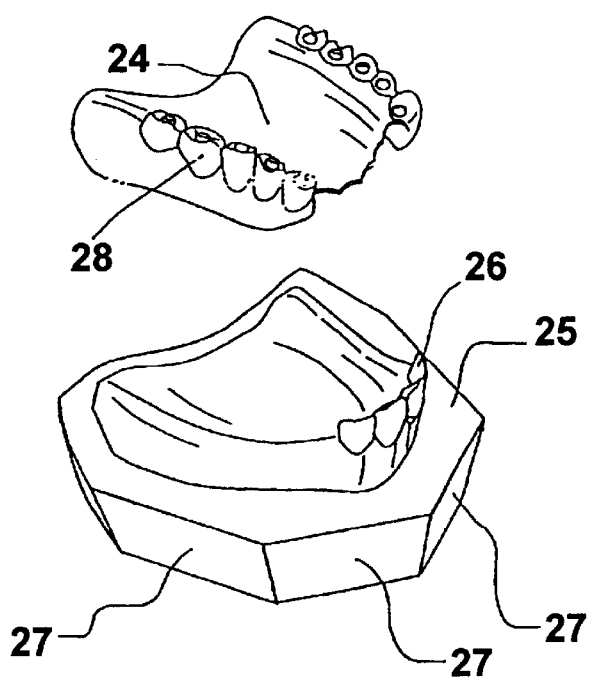
FIG. 3A shows a perspective view of the pre-tomographic guide having radio opaque elements and FIG. 3B shows a perspective view of the finished surgical template.
Figure 3B:
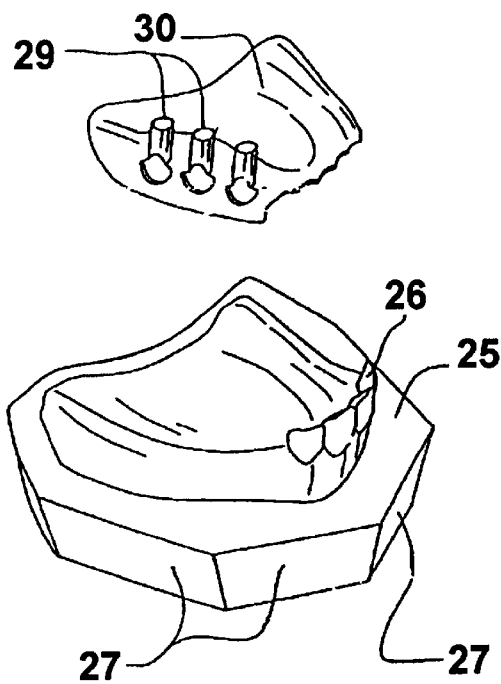

According to the above explanation and drawings, we see that the proposed device (1) comprises a rigid metal base (2), a supporting column (3) perpendicularly projecting therefrom, which on its side, supports a arm (4) having upward and downward motion with an attachment mechanism, having a bi-directional head (5) on the free end (4') thereof. It is with this head that the angular measurement of the implant is made and further attached, as hereinafter explained.

On the end opposite to the fixation of the supporting column (3), said base (2) has a fixing device which firmly retains the plaster mouth model, or a model made in a similar material, on which the duplicate of the prosthesis is seated, the prosthesis fabricated of a polymeric material, such as acrylic or similar, which also allows for the reproduction of the original position as many times as necessary.

In an embodiment, a fixing device comprises a solid metal cylindrically-shaped member (6), the member presenting on the upper face of the perimeter thereof marks of the corresponding angle positions at 360 degrees (6a) y, in the center, a cavity with the shape of a truncated polygonal prism (6b), which allows for the model to be easily removed.

In said pyramid truncated opening, a plaster mix—or a mix made from any equivalent material—and water are poured, and before setting, attaches to the model of the patient mouth, made of the same material, so they make an integrally formed member, further on, the duplicate made of polymeric, acrylic type material intended for perforation, is mounted.

This cylindrical member (6) has free rotation in a central, cylindrical hole (7a) of a metal square-shaped bottom plate (7), which is also compact and has a reference mark on the perimeter of said hole (7b), the mark is useful as an indication of the selected angle value when the hole is drilled. Said selected angle is maintained fixed by means of a binding screw (7c) or any other suitable fixing means.

On its side, the bottom plate (7) is securely mounted on the base (2) of the device by means of a longitudinally slidable carriage (8), using a pair of parallel guides (8a and 8a') on said base (2), which presents a gridded rule (10) for determining the position of said carriage (8) on said base (2).

One of the parallel guides (8a and 8a') presents a longitudinal slide where a binding screw slides (8c), for specifying the position of the assembly on the side (2') of the base (2).

Also, carriage (8) comprises two transversal, parallel guides (8b and 8b'), where said bottom plate (7) slides inwardly, one of said guides has a ruler (9), similar to the previous one, to indicate the position of said bottom plate by a lateral mark thereon (7d).

The position of the bottom plate (7) is fixed within said carriage by a binding screw (7e), the screw sliding along a longitudinal slide in one of the transversal guides (8b and 8b').

With both rules (9 and 10) and the angle value of the scale (6a), the position of the model is specified in an exact, reproducible way, which must be so in order to meet the object of this invention.

In another preferred embodiment, the end opposite to the point where the device base column is fixed, presents a gridded zone with numbers and letters, so that each grid is determined by an alphanumeric coordinate. The bottom plate (7) is placed on the grid of said base (2) and is fixed thereon using a magnet. Following determination of fixation coordinates on said bottom plate (7), it may be repeatedly disposed in the same position in a reproducible fashion.

Regardless of the mechanism or means known in the art that may be employed, the object within the scope of the present invention is to fix the model to work on in an accurate and reproducible fashion, so that the angle measurements and coordinates serve for preparing a useful template for a correct implant which is riskless for the patient.

Said column (3) allows for the arm (4) to shift upwards and downwards, thus providing for motion parallel to the base (2).

Shifting of said arm (4) is made by means of a slide operated by an actuation head (12) and once the suitable position is achieved, it is fixed by a screw (22) This slide system usually includes an inner gear that slides over a toothed bar (13) provided on the column (3) and which will not be described in detail since it is not the subject matter of the present invention and is a well known mechanism.

In another possible embodiment of this invention, said mechanism may be simplified by a sliding assembly on the column that may be fixed with a screw at the desired point, the screw may be one similar to the screw (22), which fits on a fixation plane portion disposed thereon. Any other similar actuation means may be used, provided it renders a similar result.

Then, when the operator rotates the actuation head (12), the arm moves upwards or downwards. Arm movement will always be parallel to the base (2), since these shifts cannot present any angulation modification whatsoever, as it would modify the incidence angle of the drill, which would impair all parameters of the head (5).

Said head (5) comprises a first hub (14) rotatably attached to the end of the arm (4) in the direction as indicated by the arrows A in FIG. 1. Attached to said arm (4) and approximating to the joining edge of the end of said arm (4) and the hub (14), there is a plate (15) having an angled rule (16) marked on a side thereof, comprising a range of angles from −30.degree. to +30.degree. Said hub (14) includes a needle (17) perpendicularly fixed on the hub but tightly approximating to the joining edge between the arm (4) and the hub (14), i.e. opposite to said angled rule (16). So, when the operator makes the hub (14) to rotate relative the arm (4), said tilt shall be determined by the needle (17) shift, relative to the angled rule (16). With this rule, the operator is able to determine the mesio-distal tilt angle, as will be further explained. It is also worthwhile mentioning that said hub (14) includes a binding head (18) through which said hub (14) is loosened relative to the arm (4) and screwed again, once the binding angle is found.

Optionally, the angle may be measured using any manual, mechanical or electronic means known by the person skilled in the art, and that may be useful for efficiently logging said angle.

Attached to the hub (14), similarly as the attachment between the hub (14) and the arm (4), there is a second hub (19) which also rotates as indicated by arrows B in FIG. 1; but as it can be clearly seen in the Figure, angle shift of said hub is in an orthogonal plane relative to the shifting plane of the hub (4). Attached to the hub (14) and in close proximity to the joining edge between the hub (19) and the hub (14), there is a plate (15') a side of which has an angled rule (16'), comprising a range from −30.degree. to +30.degree. (useful for logging the mouth-palatine-lingual angle). Said hub (19), includes a needle (17') perpendicularly fixed thereon, but in close proximity to the joining edge between both hubs (14) and (19). After specifying the mesio-distal angle, the operator may specify and transfer the mouth palatine-lingual angle of the drill. Said second hub (19) presents a through hole, the diameter of which is regular or constant (20), where the engine of the drill (11) is engaged for drilling the holes in the pre-tomographic guide, according to the explanation above. Said second hub (19) presents also a binding/regulation head (21) by means of which the operator may adjust the shifting angle, similar as the head (18) does with the hub (14), as well as a screw (23) for an occasional fixation of the drill engine (11).

In the preferred embodiment shown in FIG. 1 for placing steel tubes (29) used for the surgical guide (30), a metal cylinder (rod) is used, the metal cylinder tightly fits into the hole (20) of the second hub (19), orthogonally attached to the first hub (14), which also has a tapering made by tooling of a narrower diameter equivalent to the internal diameter of the steel tube (29) used for surgical guide (30).

On the distal end of the tapered metal cylinder (or rod) a guide tube is placed (29), and the assembly of rod and guide tube is fixed in the angle position as determined by the hubs (14) and (19) orthogonally attached on the surgical template (30). Subsequently, said guide tube is fixed with a suitable adhesive. With this small tube, the incidence point and the direction where the hole has been made, may be exactly mimicked.

In another environment, the guide tube (29) is directly placed using a drill (11') for drilling the hole as a guide, while direction and incidence point are kept.

With the device (1), which has been described and shown in FIG. 1, the operator may easily put into practice the proposed method.

Figure 5:
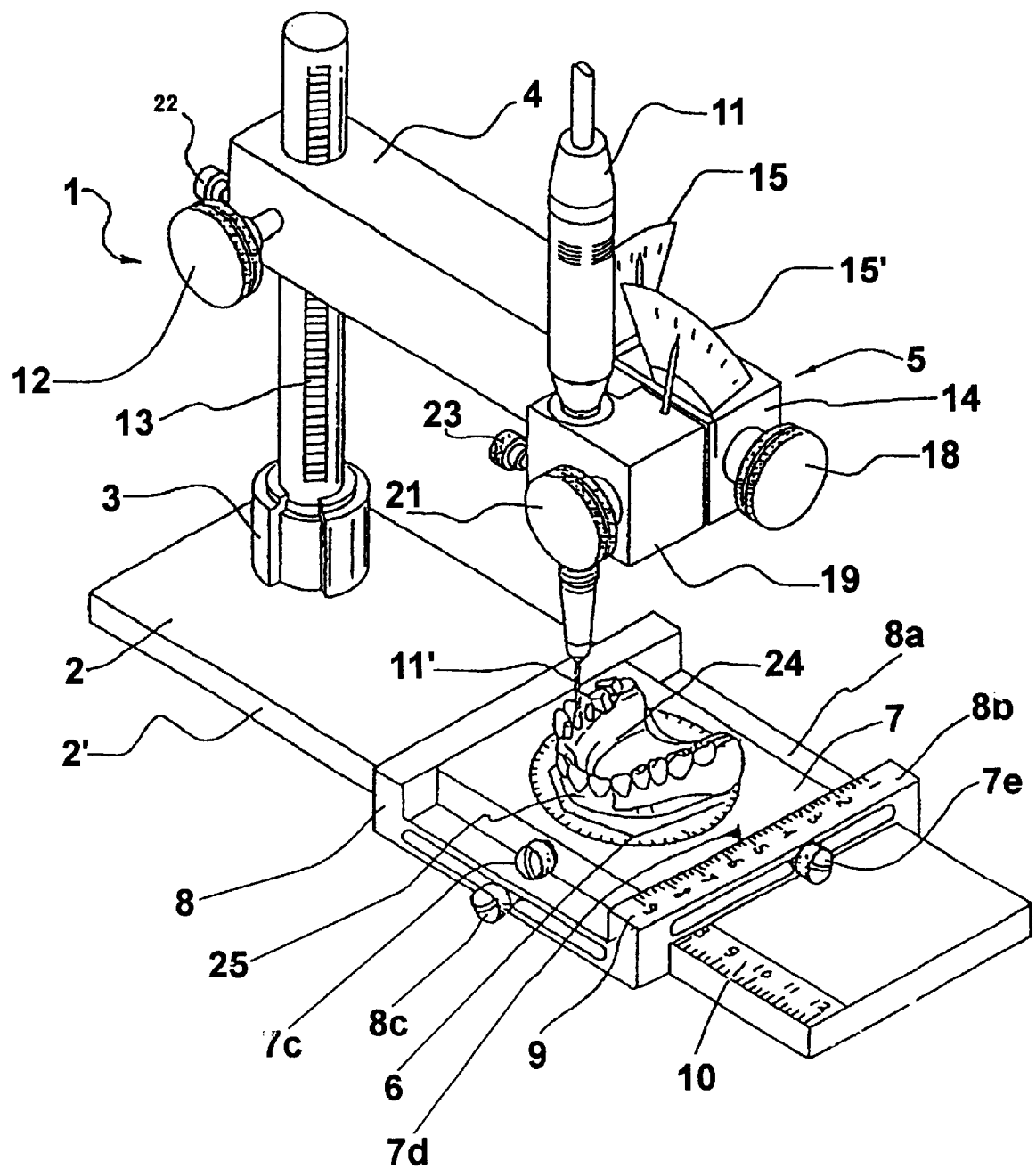
FIG. 5 is a perspective view of an embodiment of the device of present invention, showing the drilling procedure when forming the pre-tomographic guide.

Such as previously specified, this invention also provides for a method, which allows for correct placement of implants, the method comprises the following steps:

1) first, preparing a pre-tomographic guide (24) for which the following operations are performed:
   (a) an impression of the patient maxilla is taken, thus achieving a model (25), i.e. a reproduction of the patient mouth in plaster or any other similar material, comprising teeth (26) existing in the patient mouth. Afterwards, it is molded—with plaster or a similar material—to the polygonal hole (6b) from which said model takes the facetted shape (27) for its base, allowing for its placement in a reproducible fashion.
   (b) a "replica model" is prepared for evaluating the design of the future prosthesis, and it is tried into the mouth. Using a traditional duplicator, a duplication of the model is made in a polymeric material, such as acrylic or similar, which essentially consists of a replica of the future prosthesis of the same material, comprising missing teeth (28) that will implanted into the patient mouth, and it is further placed into the mouth for correctness. From this, a pre-tomographic guide (24) is made, so it is placed again in the "model" made of plaster or any other material, using the device (1) above, which allow us to drill estimate holes at the position of each dental piece in this duplicate of polymeric material, such as acrylic or similar (24), which, from the rim may coincide or not with the center of the occlusal side, in an attempt to have the direction be the closest possible to the implant, giving us a future reference point in the tomographic views. Besides, the device (1) allows us to measure randomly selected incidence angles in the mesio-distal position as well as in the mouth-palatine or lingual position of each hole. For this, the "model" (25) is placed within (6b), the assembly is supported on the base (2), and coordinates of such position are logged with the help of rules (9 and 10). Then, the engine of the drill (11) is placed in the hole (20) of the second hub (19), it is fixed with the binding screw (21) and angles are further on specified after a visual exploration of the model. The head is positioned as the hubs (14) and (19) are shifted, tightly holding the binding heads (18) and (21), once provisional incidence angles and incidence point are found, the hole is drilled as illustrated in FIG. 5.

In each step, coordinates and angles as obtained with rules and scales of the device, respectively, are logged; said log may be modified as the method proceeds, till adequate values for the implant are achieved. For positioning each possible implant the model is placed again, considering potential incidence point; coordinates of rules (9 and 10) are specified and logged, and also incidence angles are measured and logged, according to heads (14) and (19).

Later, a radio opaque substance is introduced in each hole drilled in the duplicate made of a polymeric material, such as acrylic or any other similar, the pre-tomographic guide is thus specified.

All data of each possible implant location is taken down in a sheet wherein it is stated each dental piece involved in (6b), used for drilling such a hole, on which coordinate of rules (9 and 10), to which angle corresponding to scale (6a), the model was positioned and arbitrary angles where the holes were drilled based on rules (15) and (15'). Making this guide is an enormous help, since the tomogaphy itself has a relative value, as the marks made with this device allow reference points made with this device to be transferred into the mouth, specially when working on a toothless maxilla.

Figure 4A:
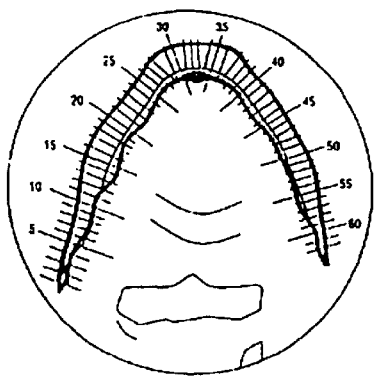
FIGS. 4A and 4B illustrate a diagram of the tomography taken, wherein a particular section is pointed, showing the maxilla bone and the direction of the radio opaque element determined in the pre-tomographic guide.
Figure 4B:
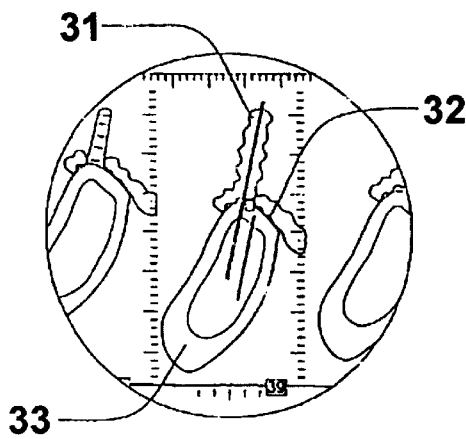

2) The second stage comprises a computed tomography with the following characteristics: it is possible to see axial parallel sections, mesio-distal or panoramic sections and a sequence of cross sections or paraxial sections spaced each other at a predetermined distance, for instance, two millimeters, such as illustrated in FIGS. 4A and 4B. The different shapes of a jaw bone (33) involved may be seen in each section. In this tomography there appears a radio opaque element (31) housed in the hole of the pre-tomography guide, as well as a horizontal portion of the radio opaque element (32) disposed on the lower part of the pre-tomographic guide, which rests on the gum tissue, so it is possible to state gingival height. Based on the element (31) it is possible to follow up these incidence points and transfer them into the mouth.

3) Computerized planning is made using a computer software where tomographic images are transferred, so accurate measurements of the bone (33) width and height are possible, so as not to injure any surrounding element when drilling the hole therein, besides allowing an easy selection of the trademark, size and shape of the implant to be used.

Afterwards, with such a computer software the placing of an implant is mimicked, which may be of the trademark, size and shape as the one to be actually used, and it is optimally placed into the bone (33), having the axis of the possible implant at sight, while it is specified whether this axis mates the axis determined with the radio opaque substance (31) of the pre-tomographic guide (24). So, the software helps in the analysis of the perfect incidence angle, and also of the suitable incidence point, and it is compared with the point determined with the radio opaque substance, and if a difference exists, it is corrected and logged in the sheet as corrected operation angle or corrected incident point, or both.

4) Having the data of the correct position finally chosen for each implant, a surgical template (30) is made, which is useful for the dentist to transfer the complete planning into the mouth. This is how the corrections are transferred into the mouth, which are logged using the above mentioned and described device. Small metal tubes are fixed on the polymeric plate, such as acrylic, which serves as a base for surgical guide, the inner diameter of said small tubes coincides with the diameter of a thickening of certain surgical drills, or even with the diameter of surgical drills which have no tubes, so the prefixed angulations may slide in these tubes and remain constant, so a hole in the jaw bone at the incidence point may be made, having corrected angulations on the patient maxilla. Such guides have corrected angulation and incidence point by the prior steps of the method.

Surgical template (30) positioned and immobilized during surgery facilitates drilling of any necessary holes through these guide tubes. It also allows to have an improved traditional surgery which is known as "exposed", since gum tissue may be marked through the surgical template, so a portion of the gum tissue may be removed according to the implant diameter (which would be marked having the template placed in the mouth), and further as the template is positioned again, holes are drilled having the necessary depth, while gingival height is measured and added.

Thus, this method is useful for both, surgeries having flaps (or "exposed"), or without flaps (or "unexposed"), since it is useful for planning and transferring into the mouth the best location for an implant.

It is understood that using a very simple device and applying also a simple, available method, the setting where implants are placed is highly improved, as already explained, and specified in the appended claims.

The teachings herein may be modified using equivalent mechanical assemblies or using suitable materials for this purpose, which will be easily apparent for the person skill in the art; all of these modifications are encompassed in the object of the present invention herein explained and protected.

What is claimed is:

1. A device for planning and further placing a dental implant, the device comprising a rigid base with a binding mechanism and a mechanism for controlling the position of a mouth model for a patient, a column projecting from said base with a regulating mechanism for the height and support of a bi-directional head comprising two hubs, the hubs being rotatably disposed in planes that are orthogonal relative to each other, with binding mechanisms for fixing certain positions, being furnished with a device for indicating the angle position of each hub relative to a specific position, one of the hubs being furnished with a drill and also a device for fixing one or more guides.

2. The device as set forth in claim 1, wherein said regulating mechanism for height regulation comprises a toothed bar and a gear, both disposed on the column perpendicular to said rigid base from which an arm projects parallel to said base, the end of the arm being associated to said bi-directional head.

3. The device as set forth in claim 2, wherein said head comprises a first hub, the hub being rotatably associated to the arm, and a second hub rotatably associated to the first hub, wherein both have binding mechanisms and mechanisms for controlling the position.

4. The device as set forth in claim 3, wherein the drill and the binding mechanism for the guides are removable, and are mounted on a cylindrical hole of the second hub and are axially concentrical relative to said cylindrical hole.

5. The device as set forth in claim 1, wherein said binding and control mechanisms on the rigid base comprise:
- a solid, metal cylindrically-shaped member, the member presenting on the upper face of the perimeter thereof marks of the angle positions corresponding to 360 degrees and, in the center, a cavity with the shape of a truncated polygonal prism;
- a solid, metal bottom plate of a square shape, which has a cylindrical central hole with a reference mark on the perimeter thereof, said hole houses said cylindrical member, further comprising a binding screw on one side thereof;
- a carriage comprising two bottom guides, the guides are longitudinal relative to said base, at least one guide comprises a longitudinal slide comprising a binding screw therein; and a pair of upper guides which are transverse parallel, between which said square-shaped bottom place is located; one of said guides comprises a transverse rule on the upper side thereof, which is used for specifying the position of said bottom plate by means of a lateral mark thereon; and also at least one guide presents a longitudinal slide comprising a binding screw inside thereof;
- a longitudinal gridded rule disposed on the base for specifying the position of said carriage on said base.

6. The device as set forth in claim 1, characterized in that the drill comprises an engine-driven mill.

7. The device as set forth in claim 1, wherein the device for fixing one or more guides comprises a rod having a cylindrical end, which diameter fits into the inner diameter of each of the one or more guides.

8. A method for planning correct placing of one or more dental implants, comprising the steps of:
- a) preparing a pre-tomographic guide by preparing an impression of the patient's mouth made of any suitable material, preparing with said impression a model of the patient's mouth, preparing on said mouth model a scale model for diagnosis, preparing a duplicate of said scale model, placing the scale model on said mouth model and drilling holes at the position of each dental piece, logging the incidence point and the incidence angles, both mesio-distal and mouth-palantine or lingual and the mouth model position, introducing a radio opaque substance in each hole;
- b) taking a computer tomography of the patient's mouth with the pre-tomographic guide placed therein, thus obtaining a tomography with marking corresponding to the radio opaque substance of the pre-tomographic guide;
- c) preparing surgery planning for observing sectional views of the patient's upper or lower jaw bone rim and comparing the incidence points and the incidence angles of each of said marking with respect to the incidence points and incidence angles at the desired position of each implant to be placed in the patient's mouth, in order to confirm or change these parameters and further logging their final values, and finally
- d) preparing a surgical template for carrying out in the patient's mouth the result of the surgical planning with said final logged parameter values by fixing one or more guides on the template, fixing with a guide in each position where an implant will be placed, with the final incidence point and incidence angle logged parameter values.

9. The method for planning correct placing of one or more dental implants as set forth in claim 8, wherein the method further comprises the step of marking the tissue gum in the place of the implant using the surgical template; removing the template and cutting a round portion of tissue gum, the portion having a diameter similar to the diameter of the hole necessary for the implant, till maxilla bone is reached; applying the surgical template and drilling the maxilla bone according to the guide of the surgical template.

10. The method for planning correct placing of one or more dental implants as set forth in claim 9, wherein the hole in the maxilla bone is made with a drill having a portion, mating the inner diameter of the guide tube of the surgical template, which allows for the drill to be centered relative the guide tube.

\* \* \* \* \*